United States Patent [19]

Fischer

[11] Patent Number: 4,656,872
[45] Date of Patent: Apr. 14, 1987

[54] WRAP-AROUND BEND TEST METHOD AND APPARATUS

[76] Inventor: Glenn N. Fischer, c/o Fischer Engineering Company, 7595 E. Singer Rd., Dayton, Ohio 45424

[21] Appl. No.: 851,743

[22] Filed: Apr. 14, 1986

[51] Int. Cl.⁴ .............................................. G01N 3/20
[52] U.S. Cl. ...................................................... 73/850
[58] Field of Search .................. 73/849, 850, 851, 854

[56] References Cited

U.S. PATENT DOCUMENTS

| | | | |
|---|---|---|---|
| 2,934,945 | 5/1960 | Geenen et al. | 73/854 |
| 3,500,679 | 3/1970 | Smith | 73/850 |
| 3,906,784 | 9/1975 | Coulstring | 73/850 |
| 4,425,802 | 1/1984 | Sponseller | 73/850 |
| 4,573,360 | 3/1986 | Yoneda | 73/850 |

FOREIGN PATENT DOCUMENTS

| | | | |
|---|---|---|---|
| 0946178 | 4/1974 | Canada | 73/854 |
| 0920942 | 12/1954 | Fed. Rep. of Germany | 73/850 |
| 0805113 | 2/1981 | U.S.S.R. | 73/850 |

Primary Examiner—Jerry W. Myracle
Assistant Examiner—Robert R. Raevis
Attorney, Agent, or Firm—Biebel, French & Nauman

[57] ABSTRACT

A method and apparatus for testing the ductility of a weld formed within a specimen utilizes a cylindrical mandrel and roller mounted for rotation along mutually parallel axes. Relative linear movement of the mandrel and roller clamps a specimen therebetween. A shoe having a contact suface is supported and connected to the mandrel for rotational movement therewith. The shoe may be moved linearly in a direction normal to the contact surface and along a line tangential to the mandrel to place the contact surface in contact with the specimen. In carrying out the method, a rotational driving force is applied to the mandrel, whereby it and the shoe are rotated to bend the specimen about the mandrel.

16 Claims, 14 Drawing Figures

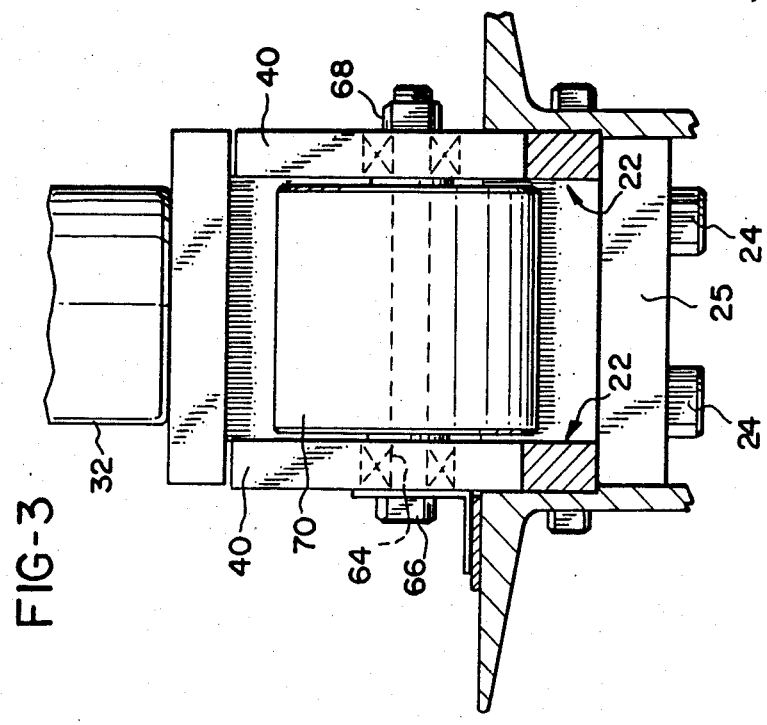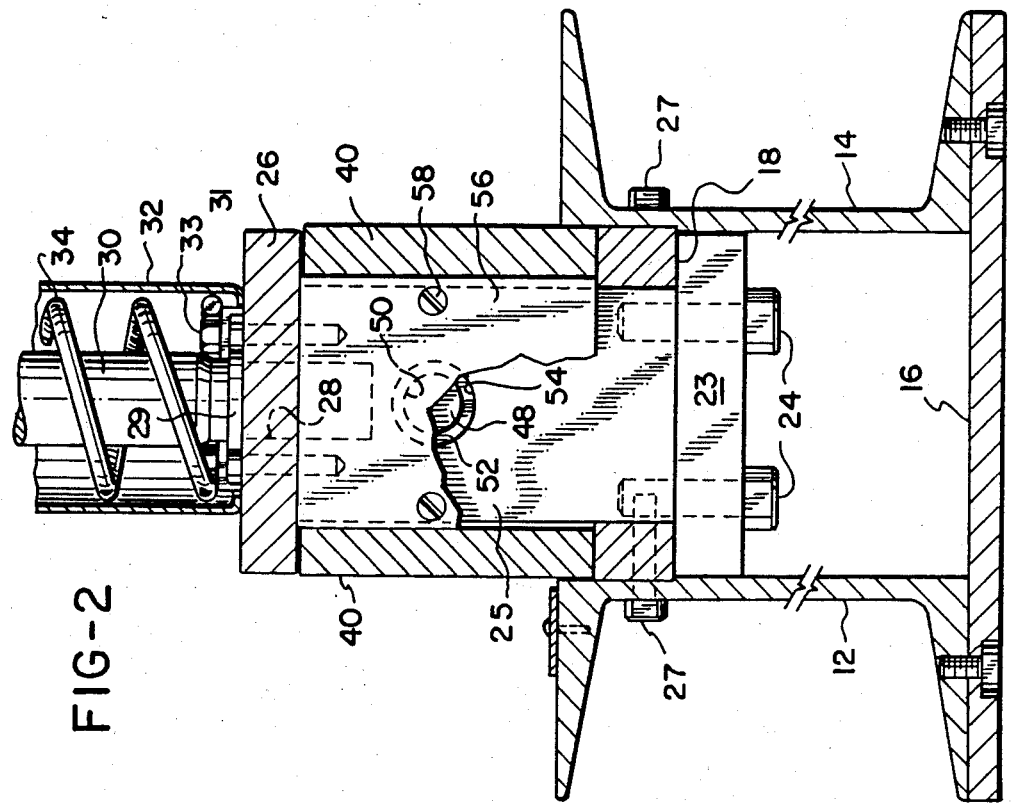

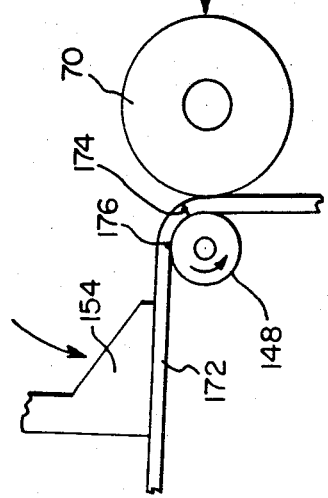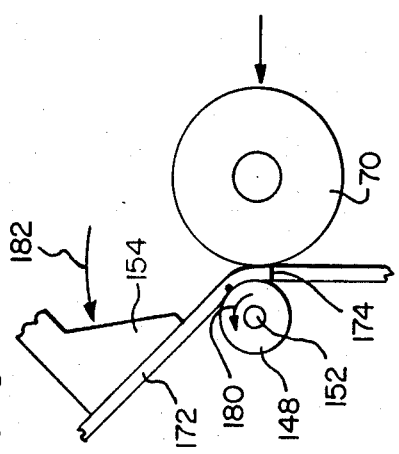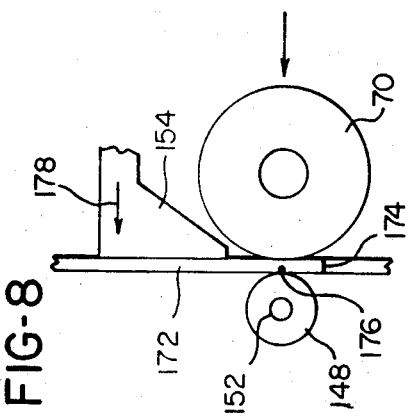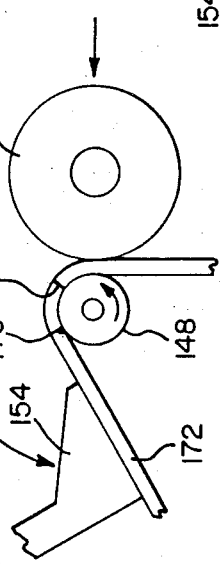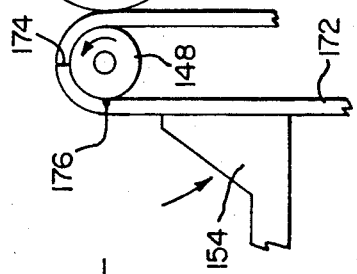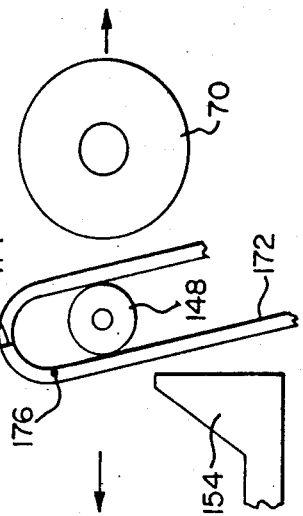

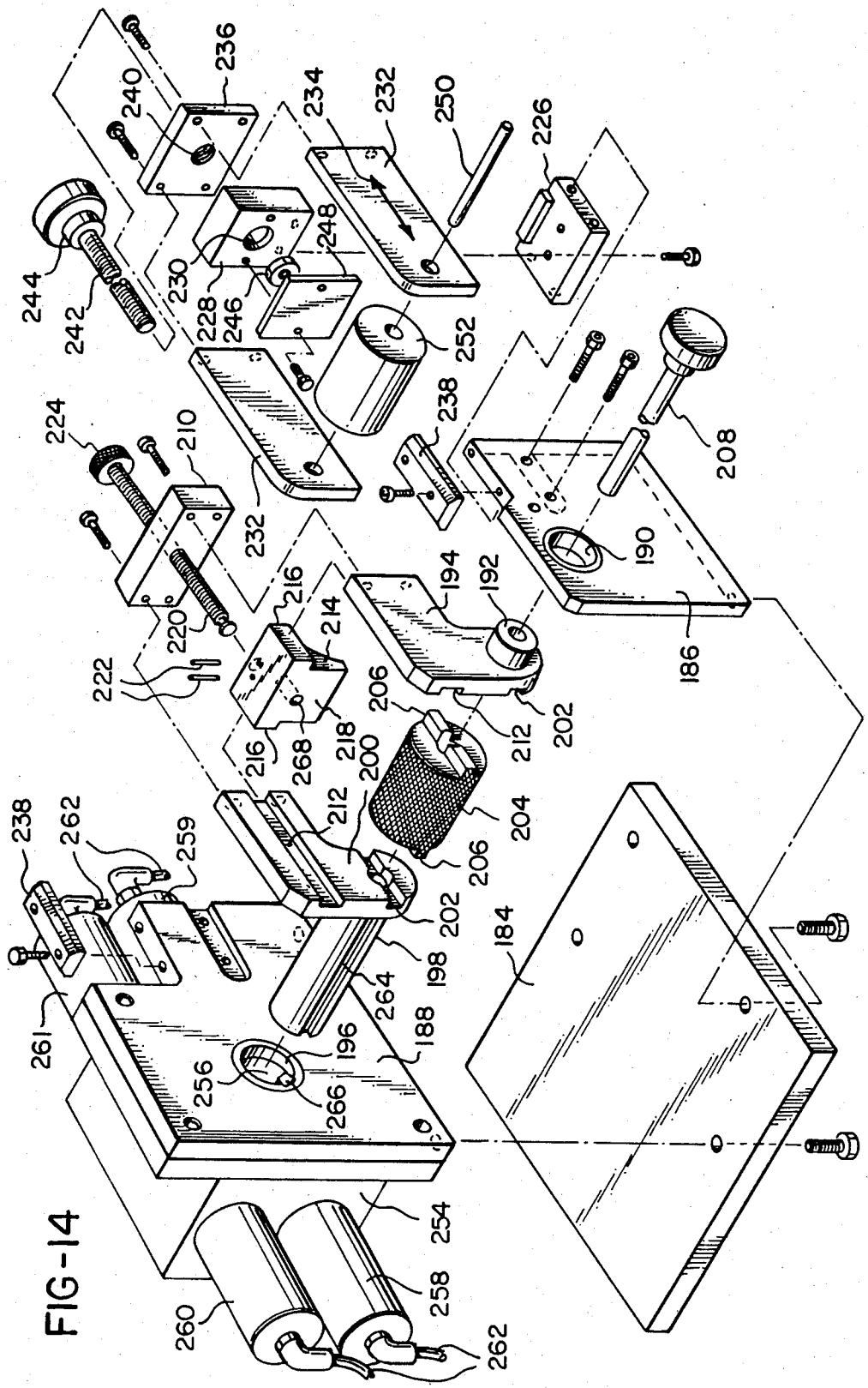

WRAP-AROUND BEND TEST METHOD AND APPARATUS

BACKGROUND OF THE INVENTION

The present invention relates generally to a method and apparatus for performing tests to determine the ductility of welds. Specifically, the test method is carried out using an apparatus to operate upon a metallic weld test specimen by subjecting the specimen, in the vicinity of the weld, to a bending force.

It is frequently desirable or necessary to test the ductility of a weld joining two pieces of similar or dissimilar metallic materials. For example, as a product is being designed that will require welding for its assembly, the characteristics and performance of particular materials and welding techniques may be tested to ensure that they possess adequate ductility in conformance with applicable codes or standards. As another example, training an individual in welding techniques or determining the individual's welding skill can be facilitated by testing the ductility of welds made.

Bend testing has been widely used in the welding industry for the purposes noted above. In performing such tests, a sample is made by welding two plates or pipes together in end-to-end fashion. Single bar specimens are then cut from the sample in such a way that the weld is positioned either transversely or longitudinally to the length of the specimen. The test is then performed by attempting to bend the specimen through 180° about a given radius. The extent to which the specimen may be bent without breaking along the weld is indicative of the weld ductility. An acceptable weld will be capable of being fully bent, although other defects present in the weld may be identified by examination of the bent specimen.

A known device for performing a wrap-around bend test is shown in U.S. Pat. No. 3,906,784, issued Sept. 23, 1975 to Coulstring. A clamp is positioned on a horizontal base with one end of the test specimen being secured in the clamp. A roller pair assembly, with the rollers having parallel axes of rotation, is mounted to the base with the axes extending vertically from the base. The roller pair assembly is further mounted for rotational movement around one of the roller pair axes. The position of the other roller is adjustable, so that after one end of the specimen is clamped in place, the welded portion may be positioned between the rollers with the rollers in contact with the specimen. The roller assembly is then rotated, with the one roller bending the specimen about the other.

By requiring a horizontal surface on which the test is carried out, the Coulstring apparatus represents a rather bulky piece of equipment. Further, during the bending operation, the sample will be subject to forces tending to pull it from the clamp attached to one end of the sample. Thus, the clamping mechanism must be capable of significant clamping force which must be carefully and firmly applied.

A second type of guided bend test may be performed by supporting the specimen in a horizontal orientation at its ends. A mandrel is lowered into contact with the central portion of the specimen, and force is applied to the specimen to cause it to bend. It may be desirable to perform both wrap-around and mandrel-type guided bend tests at the same location. In such cases it would be particularly desirable to utilize a wrap-around test apparatus which could form an attachment for an overhead-type guided bend test apparatus.

What is needed therefore, is an improved wrap-around bend test apparatus which can be made relatively compact and of relatively simple design and operation. If desired, the bend test apparatus should be capable of configuration as an attachment to other bend test equipment.

SUMMARY OF THE INVENTION

The present invention, in meeting the foregoing needs, provides a method of performing the wrap-around bend test and an apparatus specially adapted to carry out the test. The method of testing the ductility of a weld is performed upon an elongated specimen including a weld, taken from a sample formed by two plates or pipes connected by welding in end-to-end fashion.

The method includes positioning the specimen against the outer surface of a cylindrical mandrel that is mounted for rotation along a first axis. A cylindrical roller is linearly moved into contact with the specimen on a side thereof opposite the mandrel. The roller is mounted for rotation along a second axis disposed parallel to the first axis.

The contact surface of a shoe is moved into contact with the specimen along a side of the specimen opposite the mandrel and remote from the roller. The mandrel and the shoe are then rotated about the first axis, whereby the shoe bends the specimen about the mandrel.

The method may include selecting the mandrel from a plurality of mandrels of differing radial size. Further, the roller may be moved into contact with the specimen with sufficient force to clamp the specimen between the mandrel and the roller. As an alternative to this step, a hole may be drilled through the specimen at a location therealong remote from the desired location of any bending. The hole is then engaged with a pin protruding from the working surface of the shoe to secure the specimen during bending.

The apparatus for testing the ductility of a weld formed within a specimen includes a cylindrical mandrel mounted for rotation along a first axis. A cylindrical roller is mounted for rotation along a second axis disposed parallel to the first axis, the first and second axes defining a plane. Means is provided for performing relative linear movement of the mandrel and roller to move them into contact with the specimen.

A shoe defines a contact surface thereon, and means supports the shoe by connecting it to the mandrel for rotational movement therewith. Selective linear movement of the shoe within the supporting means may be produced in a direction normal to the contact surface and along a line tangential to the mandrel. Further means is connected to the mandrel and the shoe supporting means for transmitting thereto a rotational driving force. As a result, the specimen may be held between the mandrel and the roller, the contact surface of the shoe may be moved into contact with the specimen, and driving force may be applied to rotate the mandrel and the shoe supporting means to bend the specimen about the mandrel.

The mandrel may define a roughened outer surface. This roughened outer surface may in turn be produced by knurling. Alternatively, the shoe may include a pin extending outwardly from the contact surface for engagement with a hole defined in the specimen.

The apparatus may include means for removably attaching the mandrel to the base.

The apparatus may include a slide frame mounted on the base for selective sliding movement toward and away from the mandrel. The cylindrical roller is attached to the slide frame for rotation along its second axis parallel to the first axis. The slide frame includes a pair of parallel side members, the roller being connected between the side members.

The shoe supporting means may include a pair of shoe supporting plates, each of the plates being connected to one end of the mandrel, the shoe being supported between the shoe supporting plates. Each of the shoe supporting plates defines an elongated slot defined into an inner surface thereof, with the slots extending along the shoe supporting plates in a direction tangential to the mandrel. The shoe defines a pair of keys thereon, with each of the keys being fitted into one of the slots.

The means for transmitting driving force may include a shaft connected to one end of the mandrel to extend outwardly therefrom along the first axis. The shaft may define a hexagonal cross section, in which case, rotational force may be applied manually using a wrench. Alternatively, the means for transmitting driving force may include a hydraulic rotary actuator, the actuator being drivingly connected to the shaft. Other drive means are also useable.

Accordingly, it is an object of the present invention to provide a wrap-around bend test method that can be performed by an improved wrap-around bend test apparatus; to provide an improved wrap-around bend test apparatus for carrying out the method which can be made relatively compact and of relatively simple design and operation; to provide such an apparatus for use in bend testing which can firmly secure the test specimen throughout the bending operation; to provide such an apparatus which may be used as an attachment to other bend test equipment; to provide such an apparatus which can be actuated manually or by a powered drive mechanism; and to provide such an apparatus which is capable of use with a broad variety of test specimen materials and sizes.

BRIEF DESCRIPTION OF THE DRAWINGS

FIG. 2 is a sectional view of the lower portion of the apparatus of FIG. 1, taken generally along line 2—2 of FIG. 1;

FIG. 3 is an additional sectional view of the lower portion of the apparatus of FIG. 1, taken generally along line 3—3 of FIG. 1;

FIGS. 8–13 is a series of schematic views illustrating the performance of the bend test method and the operation of the apparatus in performing the method;

FIG. 14 is an exploded three-quarter view of an alternate embodiment for the apparatus of the present invention.

DETAILED DESCRIPTION OF THE PREFERRED EMBODIMENTS

Figure 1:
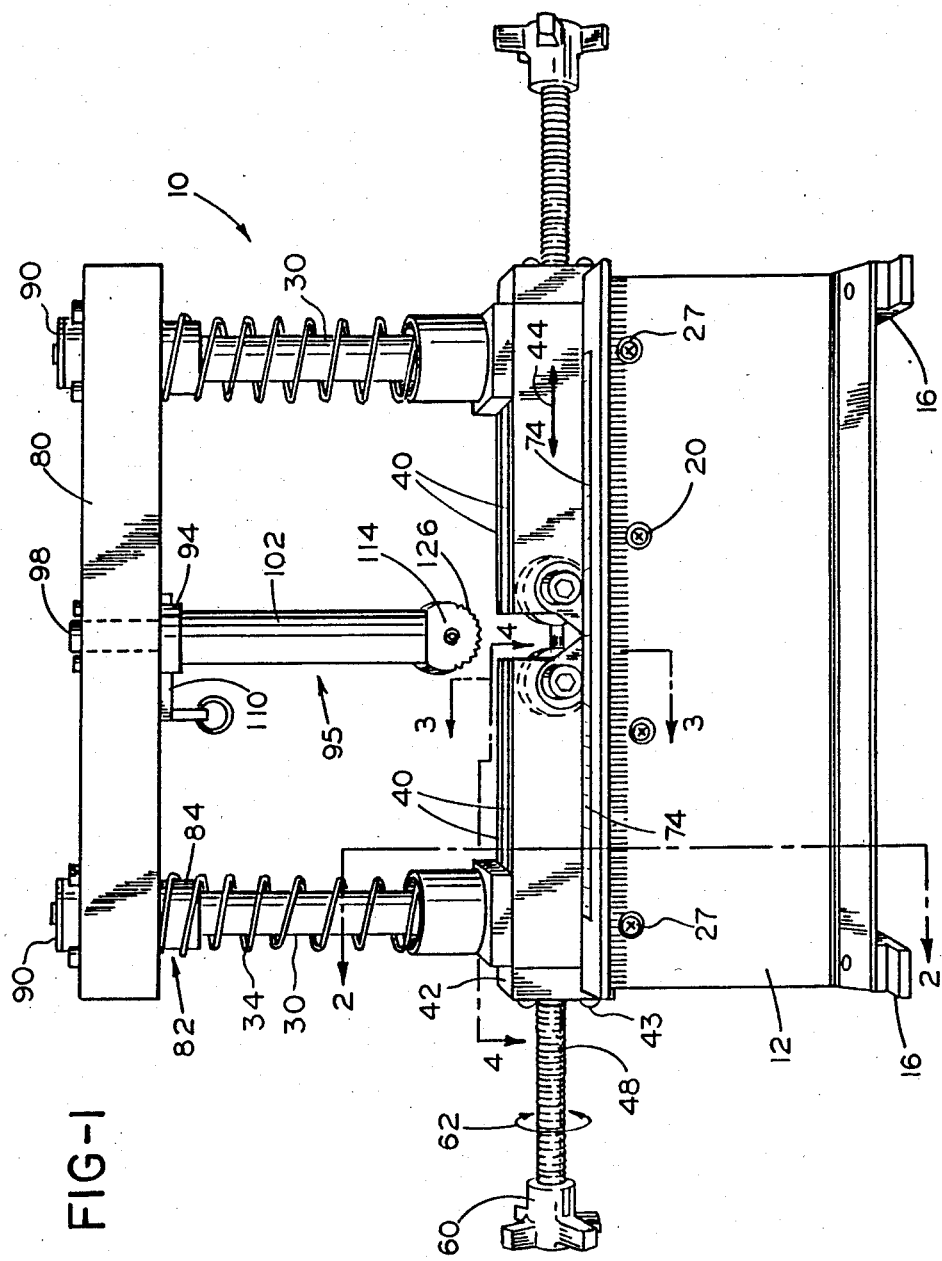
FIG. 1 is a front perspective view of an overhead guided-bend test apparatus with which one embodiment of the apparatus of the present invention may be used.

In one preferred embodiment, the wrap-around bend test apparatus of the present invention may be formed as an attachment for use with an overhead guided bend test apparatus. One appropriate overhead apparatus is shown in greater detail in my copending U.S. patent application Ser. No. 851,199, filed on even date herewith. Such a test apparatus is shown in FIG. 1, and is adapted for use with a separate device having a ram that is capable of being raised and lowered away from and toward a bed. Such an outside apparatus may be a hydraulic press or tensile/compression testing machine.

The apparatus 10 shown in FIG. 1, as well as other embodiments of the invention to be described below, must be sufficiently rigid to withstand forces exerted upon it during performance of the bend test. Thus, the various components of the apparatus 10 are formed from a rigid material, preferably a metallic material, and most preferably steel.

The apparatus 10 includes forward and rearward frame portions 12 and 14 (see also FIG. 2). These portions may be lengths of relatively shallow U-shaped channel. Frame portions 12 and 14 are connected at their lower ends by a pair of cross members 16. As shown in FIG. 3, a pair of inner slide rails 18 are connected by bolts 20 between portions 12 and 14 near, but slightly below, their uppermost ends. Rails 18 extend the full length of frame portions 12 and 14. Thus, rails 18 together define an upper work surface for the apparatus base, and in fact may be considered as part of the base. As seen also by reference to FIG. 3, the space between rails 18 is open, whereby a central opening 22 is formed, opening into the central region between frame portions 12 and 14.

One of two blocks 25, shown in FIG. 2, is mounted between rails 18 at each end of the rails, secured by bolts 27 passing through frame portions 12 and 14 and rails 18. A lower plate 23 is connected by bolts 24 to the bottom surface of each block 25. A retaining plate 26 is in turn secured to the top surface of each block 25.

A circular bore 28 is formed through each plate 26 and extends partially into each block 25. An upwardly extending cylindrical post 30 is fittable within each bore 28. A flange 29 is formed near the lower end of post 30, so that the flange is located against plate 26 when post 30 is positioned into bore 28. Clips 31 and bolts 33 cooperate with flange 29 to secure post 30 and plate 26 to block 25. A retaining cup 32 is positioned on the upper surface of plate 26, and a coil spring 34 is placed over post 30, with its lower end contained within cup 32.

Two pairs of parallel slide members 40 are positioned on inner slide rails 18, with one pair of slide members 40 located at each end of the apparatus 10. As best shown in FIG. 2, each slide member 40 of the pair is located on one rail 18 adjacent to one of the frame portions 12 and 14. As shown in FIG. 1, at the outer end of apparatus 10, the members 40 of each pair are connected by an end plate 42 attached to members 40 by screws 43.

Referring again to FIG. 2, members 40 are of a width sufficient to fit between frame portions 12 and 14 and block 25. Further, each member 40 is of a height sufficient to fit between rail 18 and retaining plate 26. Each sliding member is further sized to fit closely within the boundaries defined by inner rail 18, frame portion 12 or 14, block 25 and plate 26, but is not fitted particularly snugly into this area. Thus, each pair of members 40 may be slidably moved in a lateral direction along rails 18, as indicated by arrows 44 in FIG. 1.

A threaded bore (not shown) is formed through the center of each connecting plate 42, and a threaded shaft 48 is engaged with the threaded bore. A smooth bore 50 (FIG. 2) is formed through block 25, having a diameter slightly greater than that of shaft 48. A nut 52 is welded or otherwise attached to the end of shaft 48, and bore 50 is provided with a widened portion 54 into which nut 52 is fittable. Nut 52 and portion 54 thus cooperate to secure shaft 48 from movement outwardly with respect to block 25. A plate 56 is attached to block 25 by screws 58, thereby securing shaft 48 from movement in the opposite direction.

An appropriate handle 60 (FIG. 1) is fixedly connected to the outer end of shaft 48. Shaft 48 rotates within but is positionally fixed with respect to block 25, which is in turn fixed to frame portions 12 and 14. Shaft 48 is threadingly engaged with plate 42, which is in turn connected to sliding members 40, which are free to slide with respect to frame portions 12 and 14. An operator of apparatus 10 may grip handle 60 for rotation of shaft 48 in either direction, as indicated by arrow 62. This will result in movement of sliding members 40 either inwardly or outwardly with respect to apparatus 10.

As best seen in FIG. 3, each sliding member 40 of each pair is provided, at its end opposite from plate 42, with a transverse bore 64. A bolt 66 is passed through each bore 64 of the pair of sliding members 40, and is secured by nut 68. Bolt 66 thus defines a shaft on which are supported bearings 69 and a cylindrical roller 70 which extends between the sliding members 40. Bolt 66 and nut 68 are provided for relatively easy removal, so that roller 70 may be removed and relatively easily interchanged for a different roller.

Referring now back to FIG. 1, each post 30 extends upwardly from the base of the apparatus toward one end of a cross beam 80 having a length substantially identical to that of frame portions 12 and 14. A guide collar 82 includes a tubular portion 84 which defines an inner opening slightly larger than the diameter of post 30, so that collar 82 is slidable along post 30. Spring 34, located on post 30, fits around the exterior portion 84, with the upper end of spring 34 abutting against cross beam 80.

Because collar 82 is slidable along each post 30, beam 80 is similarly capable of relative vertical movement along posts 30. An appropriate surface member 90 is attached to the top of each post 30, so that while spring 34 normally urges collar 82 and beam 80 upwardly along post 30, surface member 90 acts as an upward stop.

A mandrel retainer 94 is secured to the lower surface of beam 80 and has an upper knob 98 extending through cross beam 80. Attached to retainer 94 is an elongated mandrel body 102. Body 102 defines the largest portion of downwardly extending mandrel 95, and is attached to retainer 94 by a pin 110 engageable with an opening (not shown) extending through both retainer 94 and an upper pin-like portion (not shown) of body 102 located within support 94. An end member 114 defines a curved, substantially cylindrical knurled or roughened working surface 126 at the lower end of mandrel 95.

Briefly, the operation of the apparatus 10 for performing the overhead guided bend test includes selecting a proper dimension for rollers 70 and member 114 in accordance with established industry standards. The proper rollers are installed between slide members 40 and the proper spacing between rollers 70 is established by adjusting the positions of slide members 40 using handles 60 connected to threaded rods 48. The proper end member 114 is attached. The test specimen is then placed on the rollers 70, with the weld centered horizontally between the rollers. The ram of the external mechanism is placed in contact with and applies force to upper knob 98 of member 94, thereby transmitting a downward driving force to member 114, which in turn contacts the specimen. Further application of force drives member 114 against the specimen, causing it to bend downwardly between the rollers 70. This causes the specimen to bend until it is formed into a complete 180° bend and is ejected between frame portions 12 and 14, or until such time as the weld fractures.

As force upon knob 98 is reduced and the ram of the external mechanism is raised, springs 34 act upwardly against beam 80. Mandrel 95 is thereby raised to its original position, whereupon the apparatus 10 is ready for a next succeeding test.

Figure 4:
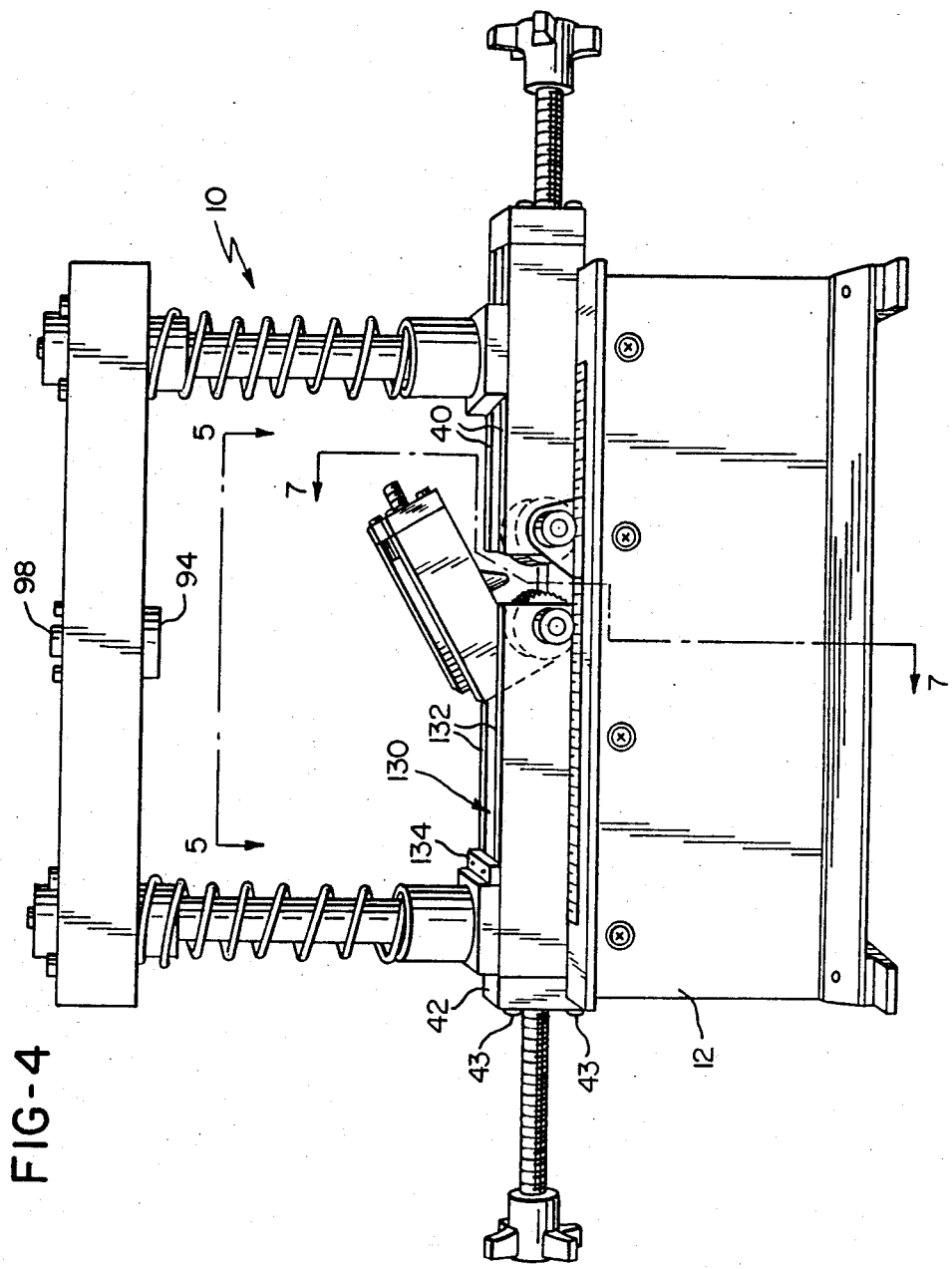
FIG. 4 is a front perspective view of the test apparatus of FIG. 1, showing the apparatus adapted by connection of an attachment to form the bend test apparatus in accordance with the present invention.

Preparation of the apparatus 10 for use as a wrap-around bend test apparatus may be seen by comparing FIG. 4 with FIG. 1. Intially, pin 110 is removed from retainer 94 and the entire mandrel 95 is detached and set aside. Next, screws 43 securing one connecting plate 42 (shown at left in FIGS. 1 and 4) to a pair of slide members 40 are removed. The slide members 40, along with roller 70 and associated portions connected thereto, are lifted away from the slide rails (not shown) supporting members 40 and taken away from apparatus 10.

Attachment 130 is placed onto the underlying slide rails (compare slide rails 18 shown in FIGS. 2 and 7) in the position formerly occupied by slide members 40. Attachment 130 includes its own pair of side members 132 which are connected by a cross member 134. Side members 132 are positioned on the slide rails, and are slid in a leftward direction in FIG. 4 until cross member 134 is located against retaining plate 26. Bolts 43 are inserted into end plate 42, which is thus secured to side members 132.

Figure 5:
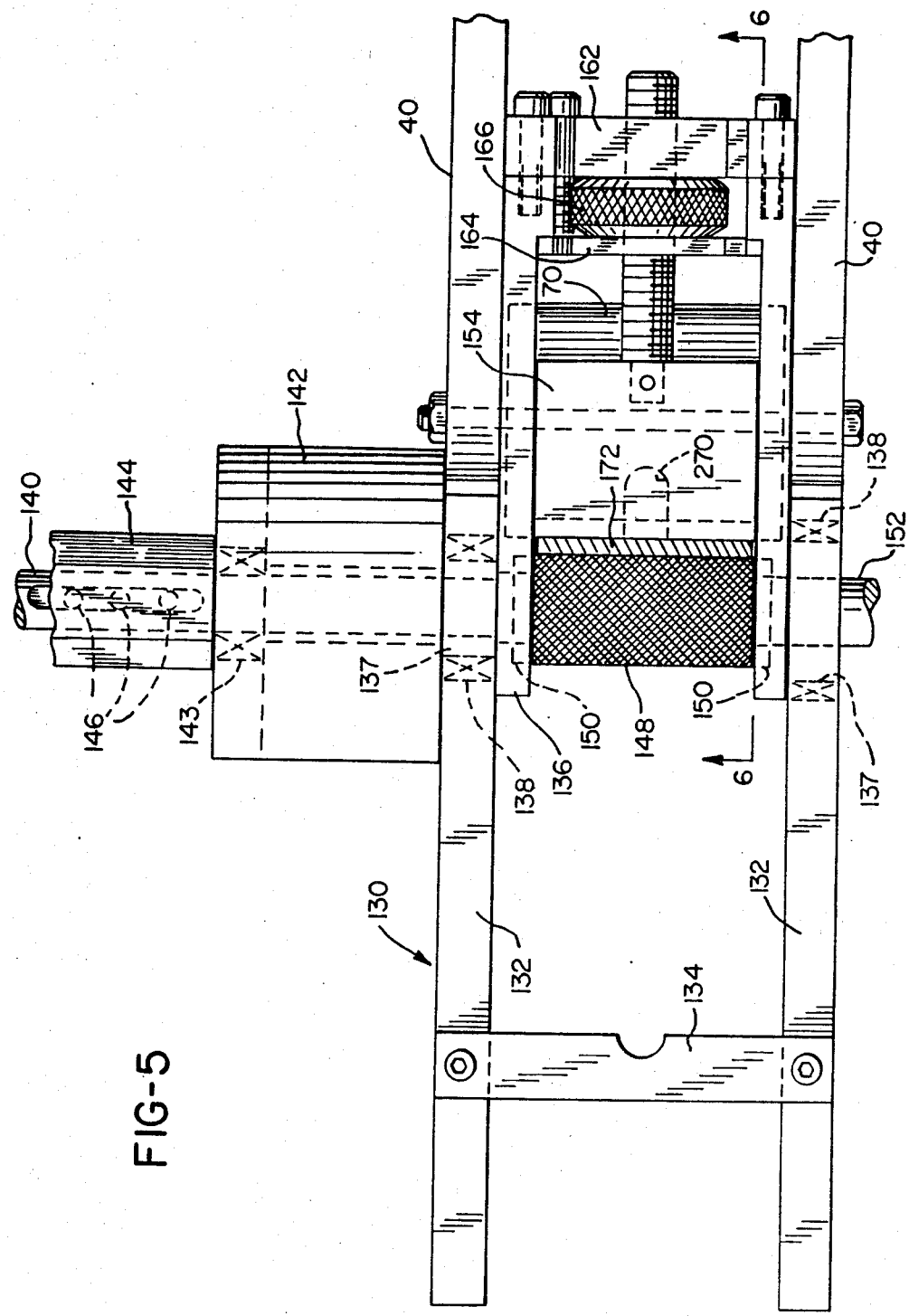
FIG. 5 is a top plan view of a portion of the apparatus of FIG. 4, taken generally along line 5—5 of FIG. 4.

Attachment 130 is shown in greater detail in FIG. 5. Additionally, the innermost portion of the non-removed slide members 40 and the corresponding roller 70 may be seen. A shoe support including support members 136 is located at the end of attachment 130 near slide members 40. Each support member 136 includes a boss 137 extending into an opening formed in adjacent side member 132, and is rotatably secured to the adjacent member 132. Each boss is also provided with an appropriate bearing 138 to ensure smooth pivotal motion.

A drive shaft 140 extends outwardly from one side member 132, and is connected for pivotal, rotational motion with shoe supporting member 136. Shaft 140 passes through a cylindrical shaft support 142 and bearings 143, within which shaft 140 is freely rotatable. A hexagonal shaft sleeve 144 is secured by screws 146 to shaft 140 beyond support 142, and is fixed to shaft 140 for rotation therewith.

Figure 6:
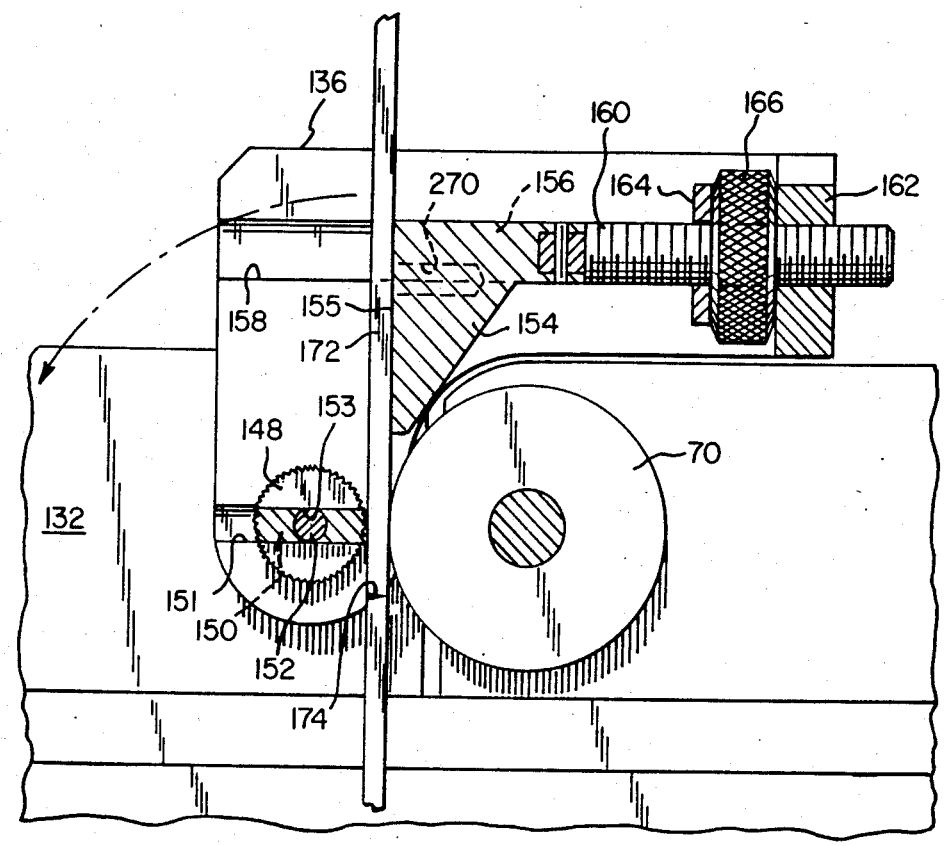
FIG. 6 is a side sectional view taken generally along line 6—6 of FIG. 5.

A cylindrical mandrel 148 is positioned between support members 136. As shown in FIG. 6, each end of mandrel 148 is provided with a diametrical key 150 cooperating with a slot 151 formed into the inner surface of each support member 136. A central bore 153 extends into mandrel 148, so that a pin 152 (see also FIG. 5) may be inserted through members 132 and 136 to secure mandrel 148 in place. Thus, mandrel 148 rotates about its cylindrical axis in conjunction with rotation of shaft 140 and pivotal movement of support members 136.

Continuing to refer to FIGS. 5 and 6, a shoe 154 having a contact surface 155 is positioned between supporting members 136. Each side of shoe 154 is provided with a key 156 fittable into a guide slot 158 formed on the inside surface of each support member 136. Shoe 154 is thereby slidable between members 136 in a lateral direction along a line tangential to cylindrical mandrel 148.

A screw shaft 160 is fixedly connected to one end of shoe 154. End plate 162 and retainer plate 164 are attached to support members 136, and shaft 160 passes through clearance holes formed in end plate 162 and retainer plate 164. A knurled thumb wheel 166 is positioned on shaft 160, in threaded engagement therewith, located between end plate 162 and retainer plate 164. Thus, rotation of wheel 166 causes lateral movement of shaft 160, which in turn results in similar movement of shoe 154 along slots 158.

Figure 7:
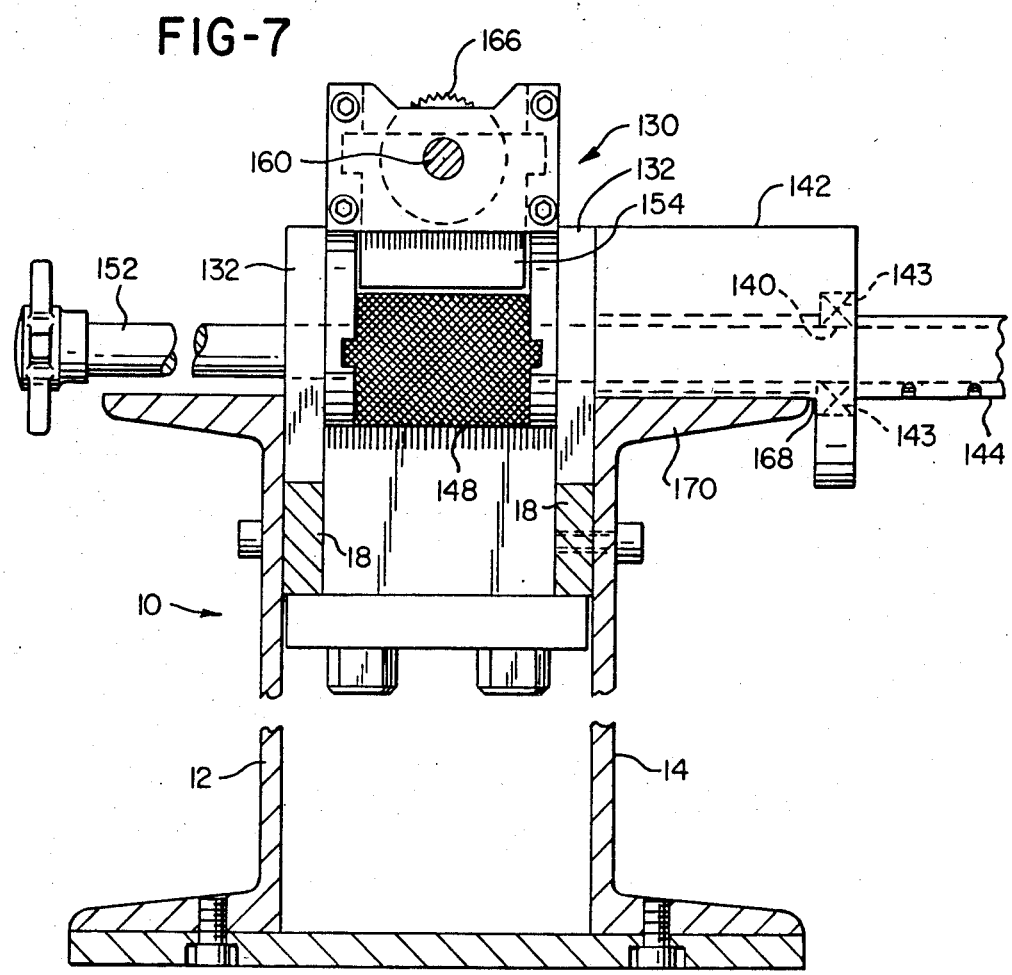
FIG. 7 is a sectional view taken generally along line 7—7 of FIG. 4.

The positioning of attachment 130 on apparatus 10 may be seen by reference to FIG. 7. Side members 132 are positioned on slide rails 18, which are connected to frame portions 12 and 14. Cylindrical support 142 is provided with a flattened cut-out portion 168, with the surface defined thereby resting on the outwardly projecting upper shelf 170 of rear frame portion 14. Shaft 140 is firmly supported by bearings 143 adjacent to hexagonal sleeve 144.

The operation of attachment 130 and apparatus 10 can be descriued by reference back to FIG. 6. In accordance with industry standards, an appropriately sized cylindrical mandrel 148 is selected and installed between support members 136. The mandrel is secured by pin 152. Any reasonably sized roller 70 may be used, since the particular radius for roller 70 is immaterial for performance of the test. An elongated specimen 172 having a weld 174 formed therein is positioned between mandrels 148 and 70. Referring briefly back to FIG. 4, the position of roller 70 is adjusted by sliding movement of slide members 40 via handle 60 until the specimen 172 is firmly held between the mandrel 148 and roller 70. Next, thumb wheel 166 is manipulated to move shoe 154 in a direction towards specimen 172 until the working face of shoe 154 is brought into contact with the specimen. At such time, the specimen is located in relation to the parts of the apparatus as shown in FIG. 6.

Referring now to FIG. 5, a driving rotational force is applied to both mandrel 148 and support members 136 through shaft 140. Since the attachment 130 is designed for use with relatively thin specimens, the driving force may be applied to shaft 140 using a wrench cooperating with hexagonal sleeve 144. The driving force applied to shaft 140 causes rotation of mandrel 148, supporting members 136 and shoe 154, all about an axis defined by pin 152.

The bending operation itself may be seen schematically by reference to FIGS. 8-13. In FIG. 8, the specimen 172 is shown positioned between mandrel 148 and roller 70. The weld 174 is positioned at a predetermined distance beneath imaginary marker 176 shown on specimen 172. Shoe 154 is adjusted in a lateral direction as shown by arrow 178 until the working surface of the shoe is positioned against speciment 172.

In FIG. 9, driving rotational force is applied to the attachment along a rotational axis coincident with pin 152. This causes rotation of mandrel 148 as shown by arrow 180, as well as pivotal movement of shoe 154 as shown by arrow 182. Rotation of roller 180 tends to move specimen 172 upwardly between mandrel 148 and roller 70, while shoe 154 forces the specimen 172 to begin bending about mandrel 148. Bending of the specimen continues as shown in FIGS. 10 and 11, until the specimen has been bent a complete 180° as shown in FIG. 12. As can be seen from marker 176, the specimen continues to move between the mandrel and roller, although it remains stationary with respect to shoe 154. This results in the weld being positioned at approximately the midpoint of the bend. Assuming that the weld formed within the specimen has been properly made, the specimen should reach the completely bent position illustrated in FIG. 12. At such time, roller 70 may be moved away, and the specimen can be lifted from mandrel 148 as shown in FIG. 13. In the event that the weld is flawed, the specimen may fracture during bending, in which case the broken pieces may fall away from the attachment or can be easily removed.

Roller 148 and shoe 154 are rotated back to the position shown in FIG. 8, whereupon the bend test apparatus is ready to begin a next succeeding test.

As can be appreciated from FIGS. 8-13, the specimen must be moved between mandrel 148 and roller 70 while the test is being carried out. Thus, it is necessary that the specimen be firmly gripped by these items. To facilitate such gripping, it is preferred that the surface of mandrel 148 be knurled, as shown in FIGS. 5 and 7, or otherwise roughened. Alternatives for a roughened surface can include a plurality of pointed pins embedded into the surface of mandrel 148. The pins may be secured by threaded engagement into mounting holes, welding, attachment with set screws, force fitting, or even cementing. Further, it should be recognized that still other alternatives for providing a roughened surface for mandrel 148 may be employed.

A second embodiment for the bend test apparatus of the present invention can be seen in exploded fashion in FIG. 14. Rather than an attachment for use with an overhead guided bend tester, the apparatus shown in Fig. 14 is an independent, stand-alone item. However, the general configuration and the operation of the apparatus of FIG. 14 is similar to that for the apparatus shown in FIGS. 4-7.

A base plate 184 has connected thereto primary front support plate 186 and rear support plate 188. Front plate 186 is provided with an opening 190 into which is positioned a boss 192 formed on the outer surface of front shoe support 194. Rear plate 188 includes an opening 196 into which is fitted an elongated shaft 198 secured in turn to rear shoe support 200.

Each shoe support 194 and 200 is provided with a lower slot 202. A cylindrical mandrel 204 includes a pair of diametrical keys 206 positioned on each end face of mandrel 204. Keys 206 may be positioned within slots 202 to locate mandrel 204 between shoe supports 194 and 200. A pin 208 may then be placed into axial bores formed in boss 192, mandrel 204 and shaft 198 for securing mandrel 204 in place.

Shoe supports 194 and 200 are connected by an end plate 210. An upper slot 212 is defined into each shoe support 194 and 200, with a shoe 214 being provided with a key 216 located on each side surface for fitting into slots 212 such that shoe 214 may be slidably moved in a linear fashion between supports 194 and 200. Shoe 214 also defines a contact surface 218.

A threaded shaft 220 has its leading end disposed within shoe 214, and is secured by pins 222 for rotation. Shaft 220 passes through and is threadingly engaged with end plate 210, and includes a thumb wheel 224 located at its outermost end. Thus, rotation of wheel 224 causes shaft 220 to cooperate with end plate 210 for advancing or retracting shoe 214 along slots 212.

Connected between front and rear support plates 186 and 188, respectively, is a slide platform 226. Secured in turn to platform 226 is a mounting block 228 having a circular bore 230 formed therethrough.

Block 228 is of less width than the spacing between support plates 186 and 188. A slide member 232 is positioned between each end of block 228 and the corresponding plate 186 or 188, with slide members 232 resting upon platform 226. Sufficient space is provided between slide members 232, block 228 and plates 186 and 188 so that slide members 232 can be moved laterally in the direction indicated generally by arrow 234. An end plate 236 is connected to the ends of members 232, whereby slide members 232 can be moved simultaneously. A cap plate 238 is secured to the top of each supporting plate 186 and 188, with cap plates 238 extending inwardly from the support plates to retain slide members 232 in position on platform 226.

End plate 236 is provided with a threaded bore 240 into which is fitted a bolt 242 including a fixed handle 244. Bolt 242 further passes through bore 230 in block 228, although bore 230 is sufficiently large to permit free rotation of bolt 242 therein. A circular nut 246 is secured, for example by welding, to the end of bolt 242, and is fittable within a widened portion of bore 230 in block 228. A cover plate 248 is secured to block 228 to retain bolt 242 in position relative to block 228. Thus, rotation of bolt 242, as a result of engagement with threaded bore 240, causes end plate 236 and slide members 232 to be moved inwardly or outwardly along platform 226.

Supported between slide members 232 is a shaft 250, which has a sliding fit with respect to members 232. A cylindrical roller 252 is positioned on shaft 250, and is mounted for rotation about the shaft on appropriate bearings (not shown).

The operation of the apparatus shown in FIG. 14 is similar to that of the apparatus shown in FIG. 4, and is identical to the operation shown schematically in FIGS. 8–13. Thumb wheel 224 is manipulated to cause threaded shaft 220 to withdraw shoe 214 toward end block 210. Bolt 242 is manipulated to withdraw roller 252 from mandrel 204. A specimen is positioned between the mandrel and roller, and bolt 242 is then moved to clamp the specimen between mandrel 204 and roller 252. Shoe 214 is then moved laterally into position by manipulation of thumb wheel 224 to cause contact surface 218 to be positioned against the weld specimen. Rotation of shaft 198 then causes the bending operation shown in FIGS. 8–13 to be performed.

To provide rotary driving force for the apparatus, a hydraulic rotary actuator 254 is mounted behind support plate 188. Actuator 254 includes a shaft-receiving opening 256 concentric with opening 196 in support plate 188. Actuator 254 is preferably a commercially available hydraulic actuator, and is more preferably a Model No. 133 Series H actuator available from Ohio Oscillator Company of Orrville, Ohio.

Actuator 254 is provided with a lower pair of opposed hydraulic cylinders 258 and 259 and an upper pair of opposed hydraulic cylinders 260 and 261. Appropriate hydraulic fluid lines 262 are connected to a control system (not shown). The actuator 254 operates when fluid is directed, for example, into cylinders 258 and 261, causing pistons therein to move inwardly with respect to the actuator. This in turn causes opposing pistons located in cylinders 260 and 259 to move outwardly. The opposing pistons are each connected by a rack gear disposed on either side of a pinion. Movement of the pistons causes movement of the rack, with the linear motion being converted to rotational movement of the pinion. The rotational movement is in turn imparted to shaft 198, which is positioned within opening 256. Shaft 198 and opening 256 are provided, respectively, with a keyway 264 and key 266 to ensure that shaft 198 is firmly secured for driving.

Of course, it will be recognized that other drive means could be used for powering shaft 198. Further, provision for hand driving, as is used with the embodiment of the invention shown in FIG. 4, is possible. Similarly, the embodiment shown in FIG. 4 could be driven by a hydraulic actuator or other drive means.

Normally, in performing the wrap-around bend test, the specimen is clamped between mandrel 204 and roller 252. Movement of the specimen during the bending operation is effected by a knurled or otherwise roughened surface of mandrel 204, in a manner identical to that of mandrel 148 in the embodiment previously described. However, as an alternative, contact surface 218 of shoe 214 may be provided with a pin-receiving opening 268. A pin 269 may be positioned within the working face, and cooperates to engage a hole drilled through the test specimen. The pin keeps the specimen firmly in engagement with the shoe during bending, thereby achieving the same results as a knurled surface on mandrel 204. Of course, it will be recognized that the pin driving method may be used with the shoe of the embodiment shown in FIGS. 4, 5 and 6. An appropriate opening 270 is shown in FIGS. 5 and 6.

Use of a pin in connection with the wrap-around bend test may be particularly advantageous where the test specimen is formed from two plates having slightly different thicknesses. In such a case, if the specimen is clamped between the mandrel and a roller along its thicker portion, much of the clamping force will be lost as the thinner portion moves between the mandrel and roller. This problem is avoided if a pin is provided for securing the specimen, since the introduction of some space between the roller and specimen will have no effect upon the bending operation.

While the methods herein described, and the forms of apparatus for carrying these methods into effect, constitute preferred embodiments of this invention, it is to be understood that the invention is not limited to these precise methods and forms of apparatus, and that changes may be made in either without departing from the scope of the invention, which is defined in the appended claims.

What is claimed is:

1. Apparatus for testing the ductility of a weld formed within a specimen, comprising:
   a cylindrical mandrel mounted for rotation along a first axis;
   a cylindrical roller mounted for rotation along a second axis disposed parallel to said first axis, said first and second axes defining a plane;
   means for performing relative linear movement of said mandrel and said roller to move said mandrel and said roller into contact with the specimen positioned therebetween;

a shoe defining a contact surface thereon;

means for supporting said shoe connected to said mandrel for rotational movement therewith;

means for producing selective linear movement of said shoe within said supporting means in a direction normal to said contact surface and along a line tangential to said mandrel; and means connected to said mandrel and said shoe supporting means for transmitting thereto a rotational driving force;

whereby the specimen may be clamped between said mandrel and said cylindrical roller, said contact surface of said shoe may be moved into contact with the specimen, and driving force may be applied to rotate said mandrel and said shoe supporting means to bend the specimen about said mandrel.

2. Apparatus as defined in claim 1, wherein said mandrel defines a roughened outer surface.

3. Apparatus as defined in claim 2, wherein said roughened outer surface is knurled.

4. Apparatus as defined in claim 1, wherein said shoe includes a pin extending outwardly from said contact surface for engagement with a hole defined in the specimen.

5. Apparatus for testing the ductility of a weld formed within a specimen, comprising:

a base;

a cylindrical mandrel attached to said base for rotation along a first axis;

a slide frame mounted on said base for selective sliding movement toward and away from said mandrel;

a cylindrical roller attached to said slide frame for rotation along a second axis disposed parallel to said first axis, said first and second axes defining a plane;

a shoe defining a contact surface thereon;

means for supporting said shoe connected to said mandrel for rotational movement therewith;

means for producing selective linear movement of said shoe within said supporting means in a direction normal to said contact surface and along a line tangential to said mandrel; and means connected to said mandrel and said shoe supporting means for transmitting thereto a rotational driving force;

whereby the specimen may be positioned between said mandrel, and said cylindrical roller, said slide frame being moved to cause said cylindrical roller and mandrel to contact the specimen, said contact surface of said shoe is moved into contact with the specimen, and driving force may be applied to rotate said mandrel and said shoe supporting means to bend the specimen about said mandrel.

6. Apparatus as defined in claim 5, further comprising means for removably attaching said mandrel to said base.

7. Apparatus as defined in claim 5, wherein said slide frame includes a pair of parallel side members, said cylindrical roller being connected between said side members, and means for causing selective sliding movement of said side members.

8. Apparatus as defined in claim 5, wherein said shoe supporting means includes a pair of shoe supporting plates, each of said plates being connected to one end of said mandrel, said shoe being supported between said shoe supporting plates.

9. Apparatus as defined in claim 8, wherein each of said shoe supporting plates defines an elongate slot defined into an inner surface thereof, said slots extending along said shoe supporting plates in a direction tangential to said mandrel, and wherein said shoe defines a pair of keys thereon, each of said keys being fitted into one of said slots.

10. Apparatus as defined in claim 5, wherein said means for transmitting driving force includes a shaft connected to one end of said mandrel to extend outwardly therefrom along said first axis.

11. Apparatus as defined in claim 10, wherein said shaft defines a hexagonal cross section.

12. Apparatus as defined in claim 10, wherein said means for transmitting driving force further includes a hydraulic rotary actuator, said actuator being drivingly connected to said shaft.

13. A method of testing the ductility of a weld formed within an elongated specimen including a weld, comprising the steps of:

positioning the specimen against the outer surface of a cylindrical mandrel mounted for rotation along a first axis;

linearly moving a second cylindrical roller into contact with the specimen on a side thereof opposite said mandrel, said second roller being mounted for rotation along a second axis disposed parallel to said first axis;

moving the contact surface of a shoe into contact with the specimen along a side of the specimen opposite said mandrel and remote from said second roller; and rotating said mandrel and said shoe about said first axis, whereby said shoe bends the specimen about said mandrel.

14. The method as defined in claim 13, comprising the further step of selecting said mandrel from a plurality of rollers of differing radial size.

15. The method as defined in claim 13, wherein said second roller is moved into contact with the specimen with sufficient force to clamp the specimen between said mandrel and said second roller.

16. The method as defined in claim 13, comprising the further steps of drilling a hole through the specimen at a location therealong remote from the desired location of any bending, and engaging said hole with a pin protruding from said contact surface of said shoe to secure the specimen during bending.

* * * * *